(12) United States Patent
Lu et al.

(10) Patent No.: US 11,727,037 B2
(45) Date of Patent: Aug. 15, 2023

(54) CONTINUOUSLY GENERALIZED ORDINAL REGRESSION

(71) Applicant: Booz Allen Hamilton Inc., McLean, VA (US)

(72) Inventors: Fred Sun Lu, Camas, WA (US); Edward Simon Paster Raff, Jamesville, NY (US)

(73) Assignee: BOOZ ALLEN HAMILTON INC., McLean, VA (US)

( * ) Notice: Subject to any disclaimer, the term of this patent is extended or adjusted under 35 U.S.C. 154(b) by 0 days.

(21) Appl. No.: 17/385,105

(22) Filed: Jul. 26, 2021

(65) Prior Publication Data

US 2023/0040110 A1  Feb. 9, 2023

(51) Int. Cl.
G06F 16/28  (2019.01)
G06N 5/04  (2023.01)

(52) U.S. Cl.
CPC ............ *G06F 16/285* (2019.01); *G06N 5/04* (2013.01)

(58) Field of Classification Search
CPC ................................. G06F 16/285; G06N 5/04
See application file for complete search history.

(56) References Cited

U.S. PATENT DOCUMENTS

| | | | |
|---|---|---|---|
| 8,423,378 B1* | 4/2013 | Goldberg | G16H 40/67 705/2 |
| 2007/0011121 A1* | 1/2007 | Bi | G06F 18/2411 706/20 |
| 2007/0092888 A1* | 4/2007 | Diamond | C12Q 1/6883 702/20 |
| 2013/0173632 A1* | 7/2013 | Birdwell | G06F 16/2246 707/743 |
| 2016/0110497 A1* | 4/2016 | Dzakula | G16B 30/00 702/20 |

OTHER PUBLICATIONS

Agrawal et al., "A rewriting system for convex optimization problems", Journal of Control and Decision, 5(1):42-60, 2018.
Agresti, Modeling ordinal categorical data, University of Florida, Department of Statistics, 2013.

(Continued)

*Primary Examiner* — Mariela Reyes
*Assistant Examiner* — Courtney Harmon
(74) *Attorney, Agent, or Firm* — Buchanan Ingersoll & Rooney PC (57) ABSTRACT

A method and system for configuring a computer for data classification using ordinal regression includes: receiving and storing a data set having data with a plurality of data features that have an ordinal relationship; generating a plurality of ordinal classification bins based on the relationship of the data features, at least one ordinal classification bin having walls defined by at least two hyperplanes; generating an ordinal regression model of the data set illustrating the data of the data set arranged into the plurality of ordinal classification bins; and tuning the slopes of the walls of the at least one ordinal classification bin based on the relationships between the plurality of data features of the data arranged within the at least one ordinal classification bin such that the slopes of the two hyperplanes defining the walls of the at least one ordinal classification bin are not parallel.

20 Claims, 4 Drawing Sheets

(56) References Cited

OTHER PUBLICATIONS

Ananth et al., "Regression models for ordinal responses: a review of methods and applications", International journal of epidemiology, 26(6):1323-1333, 1997.
Bunea et al., "Sparsity oracle inequalities for the lasso", Electronic Journal of Statistics, 1:169-194, 2007.
Cao et al., "Rank-consistent ordinal regression for neural networks", arXiv preprint arXiv:1901.07884, 2019.
Cheng et al., "A neural network approach to ordinal regression", In 2008 IEEE International Joint Conference on Neural Networks (IEEE World Congress on Computa-tional Intelligence), pp. 1279-1284. IEEE, 2008.
Chu et al., "Support vector ordinal regression", Neural computation, 19(3):792-815, 2007.
Diamond et al., "CVXPY: A Python-embedded modeling language for convex optimization", Journal of Machine Learning Re-search, 2016.
Gutierrez et al., "Ordinal regression methods: survey and experimental study", IEEE Transactions on Knowledge and Data Engineering, 28(1):127-146, 2015.
Levi et al., Age and gender classification using convolutional neural networks. In Proceedings of the IEEE conference on computer vision and pattern recognition workshops, pp. 34-42, 2015.
Li et al., "Ordinal regression by extended binary classification", Advances in neural information processing systems, 19:865-872, 2006.
Liu et al., "A constrained deep neural network for ordinal regression", In Proceedings of the IEEE Confer-ence on Computer Vision and Pattern Recognition, pp. 831-839, 2018.
McCullagh, "Regression models for ordinal data", Journal of the Royal Statistical Society: Series B (Methodological), 42(2):109-127, 1980.
Niu et al., "Ordinal regression with multiple output cnn forage estimation", In Proceedings of the IEEE conference on computer vision and pattern recognition, pp. 4920-4928, 2016.
O'Shea et al., "Over-the-airdeep learning based radio signal classification", IEEE Journal of Selected Topics in Signal Processing, 12(1):168-179, 2018.
Palermo et al., "Dating historical color images", In European Conference on Computer Vision, pp. 499-512. Springer, 2012.
Pedregosa et al., "On the consistency of ordinal regression methods", The Journal of Machine Learning Re-search, 18(1):1769-1803, 2017.
Rennie et al., "Loss functions for preference levels: Regression with discrete ordered labels", In Proceedings of the IJ-CAI multidisciplinary workshop on advances in preference handling, vol. 1, Kluwer Norwell, MA, 2005.
Rothe et al., "Dex: Deep expectation of apparent age from a single image", In Proceedings of the IEEE international conference on computer vision workshops, pp. 10-15, 2015.
Wang et al., "Tackling multiple ordinal regression problems: Sparse and deep multi-task learning approaches", arXiv preprint arXiv: 1907.12508, 2019.
Williams, "Understanding and interpreting generalized ordered logit models", The Journal of Mathematical Sociology, 40(1):7-20, 2016.

* cited by examiner

CONTINUOUSLY GENERALIZED ORDINAL REGRESSION

FIELD

The present disclosure relates to methods and systems for data classification using ordinal regression, and more particularly to continuously generalized ordinal regression.

BACKGROUND

Ordinal regression is a classification task where classes have an order, and prediction error increases the further the predicted class is from the true class. In ordinal regression problems, the prediction task is to choose the target y from a set of labels with an ordered relation, e.g., 1<2< . . . <k. Unlike in classification, where accuracy is paramount, in ordinal regression the loss generally increases as the model predicts classes further away from the true label. The standard approach for modeling ordinal data involves fitting parallel separating hyperplanes that optimize a certain loss function. This assumption offers sample efficient learning via inductive bias but is often too restrictive in real-world data sets where features may have varying effects across different categories. Allowing category-specific hyperplane slopes creates generalized logistic ordinal regression, increasing the flexibility of the model at a cost to sample efficiency. For example, consider predicting medication dosage, where adjacent dosage amounts may still be safe, but large differences in dosage can be fatal. Ordinal regression models are valuable in these applications because their predictions are more accurate to reality and furthermore, they learn more efficiently than classifiers in these situations because their inductive bias is better suited to the problem. Two existing approaches for ordinal regression are threshold-based models and generalized ordinal regression using generalized coefficients.

Figure 1A:
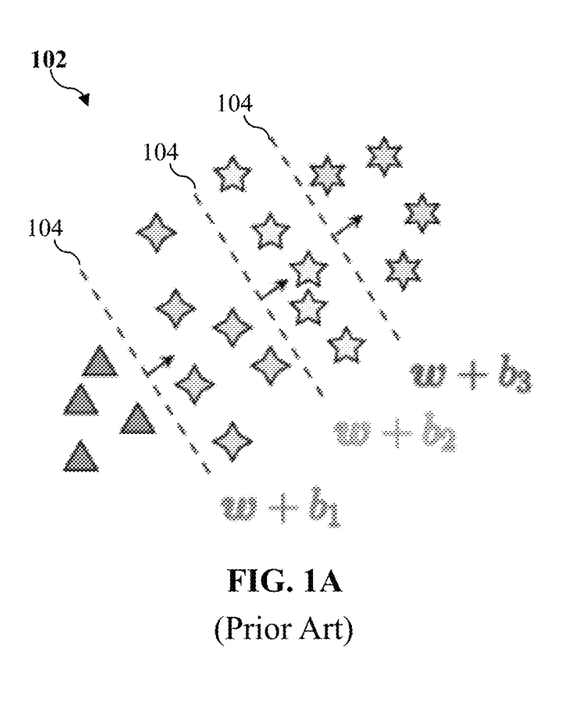
FIG. 1A is a block diagram illustrating a threshold-based ordinal regression model in accordance with the prior art.
Figure 1B:
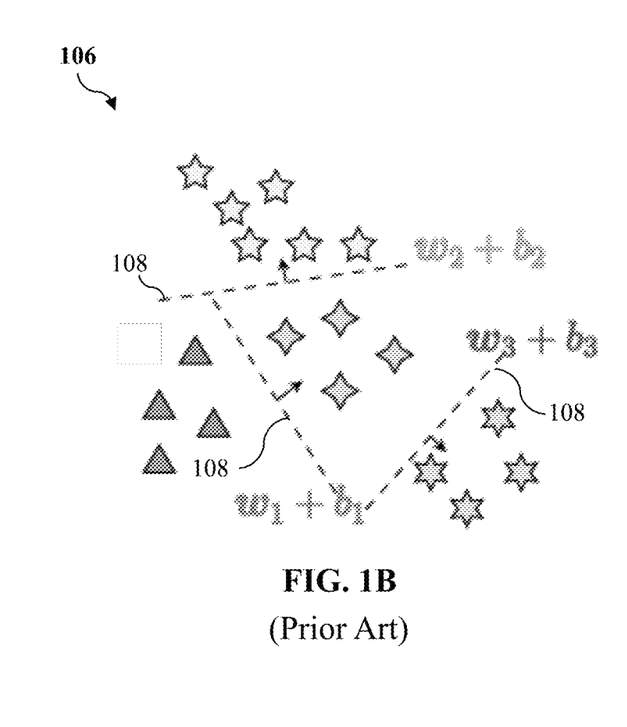
FIG. 1B is a block diagram illustrating a generalized ordinal regression model in accordance with the prior art.

Threshold-based models are one of the most widely used ordinal regression models. In such models, a single linear mapping from the features to a continuous prediction is learned, and the prediction is then partitioned into classes based on a set of thresholds. However, threshold-based models often impose unreasonably strict requirements on the nature of the ordinal relationship of the data. FIG. 1A illustrates a standard threshold-based model 102 that assumes all hyperplanes 104 are parallel, i.e. the slopes of the hyperplanes are equal. To address this restriction, some ordinal models introduce generalized coefficients for learning a separate linear mapping for each class. While this generalized ordinal regression adds much needed flexibility, it has only been explored with cumulative link loss models. These models are still rather inflexible and learn poorly on many data sets, especially when the features fall outside the expected modeling assumptions. FIG. 1B illustrates a generalized ordinal regression model 106 that makes no assumption on the relationship between the hyperplanes 108. Thus, there is a need for a novel and more flexible approach to more accurately predict data classification using ordinal regression.

SUMMARY

A method for configuring a computer for data classification using ordinal regression is disclosed. The method includes receiving and storing a data set, the data set having data with a plurality of data features, the plurality of data features having an ordinal relationship; generating a plurality of ordinal classification bins based on the relationship of the data features, at least one ordinal classification bin having walls defined by at least two hyperplanes; generating an ordinal regression model of the data set, the ordinal regression model illustrating the data of the data set arranged into the plurality of ordinal classification bins; and tuning the slopes of the walls of the at least one ordinal classification bin based on the relationships among the plurality of data features of the data arranged within the at least one ordinal classification bin such that the slopes of the two hyperplanes defining the walls of the at least one ordinal classification bin are not parallel. The method may also include: receiving a data file, the data file having one or more of the plurality of data features; inputting the data file into the tuned ordinal regression model; classifying the data file into one of the plurality of ordinal classification bins based on the one or more of the plurality data features of the data file; and outputting a data file classification prediction based on the data file classification.

A system for configuring a computer for data classification using ordinal regression is disclosed. The system includes a memory configured to receive and store a data set, the data set having data with a plurality of data features, the plurality of data features having an ordinal relationship: The system also includes a processor configured to generate a plurality of ordinal, classification bins based on the relationship of the data features, at least one ordinal classification bin having walls defined by at least two hyperplanes; generate an ordinal regression model of the data set, the ordinal regression model illustrating the data of the data set arranged into the plurality of ordinal classification bins; tune the slopes of the walls of the at least one ordinal classification bin based on the relationships between the plurality of data features of the data arranged within the at least one ordinal classification bin such that the slopes of the two hyperplanes defining the walls of the at least one ordinal classification bin are not parallel. The processor may also be configured to receive a data file, the data file having one or more of the plurality of data features; input the data file into the tuned ordinal regression model; classify the data file into one of the plurality of ordinal classification bins based on the one or more of the plurality data features of the data file; and output a data file classification prediction based on the data file classification.

BRIEF DESCRIPTION OF THE DRAWING FIGURES

The scope of the present disclosure is best understood from the following detailed description of exemplary embodiments when read in conjunction with the accompanying drawings. Included in the drawings are the following figures.

DETAILED DESCRIPTION

Currently, ordinal regression approaches can be grouped into three categories: naïve, binary classification, and threshold-based approaches. Approaches in the naïve category fit a classification model, or a regression model whose output is then discretized. Since ordinal regression falls somewhere between classification and regression, the problem benefits from more specialized approaches than the naïve approach. The binary classification approach is based on decomposing the ordinal categories into binary classification problems, whose outputs can be combined into an ordinal prediction. Threshold-based approaches simultaneously learn an output mapping and appropriate thresholds that partition the output to make ordinal predictions. For example, linear threshold models generally find the parallel hyperplanes that best separate the ordinal classes by minimizing an objective function. One current, well-known class of linear threshold models is the cumulative logit or proportional odds model, which is imbued with probabilistic interpretation as a latent continuous target variable under censoring. Among many variants of the cumulative logit or proportional odds model are the generalized ordered logit model in which one generalizes the weights to be class-dependent. However, the underlying proportional odds assumption of this class of models does not generalize well to many data sets. The linear threshold-based models utilize loss functions such as the mean absolute error and the 0-1 loss and their corresponding surrogate loss functions were named the all-thresholds and immediate-threshold loss. The difference between the two versions is that the all-thresholds loss on an (x; y) pair contains penalty terms from all ordinal classes, regardless of the value of y, while the immediate-threshold loss only contains terms from the thresholds corresponding to y. The current ordinal regression methodologies are very restrictive and inflexible when it comes to ordinal classification as well as performing poorly on data sets that include features outside the expected modeling assumptions. Exemplary embodiments of the methods and systems provided herein address these restrictions by introducing generalized coefficients to the all-thresholds ordinal loss function, which yields a more stable and flexible model. Our new continuously generalized ordinal logit (coGOL) allows interpolating between these two extreme prior approaches as shown in FIGS. 1A and 1B. By being able to adjust model flexibility, coGOL obtains better linear performance on established benchmark data sets, with competitive results in deep models as well. Exemplary embodiments of the methods and systems provided herein also introduce a regularization step that permits control over the flexibility of the model. This novel regularization step allows a bias-variance tradeoff in the model, thus combatting under- and over-fitting. Further, exemplary embodiments of the methods and systems provided herein extend the coGOL method to deep learning by attaching the coGOL model with the all-thresholds loss at the end of a neural network.

System Overview

Figure 2A:
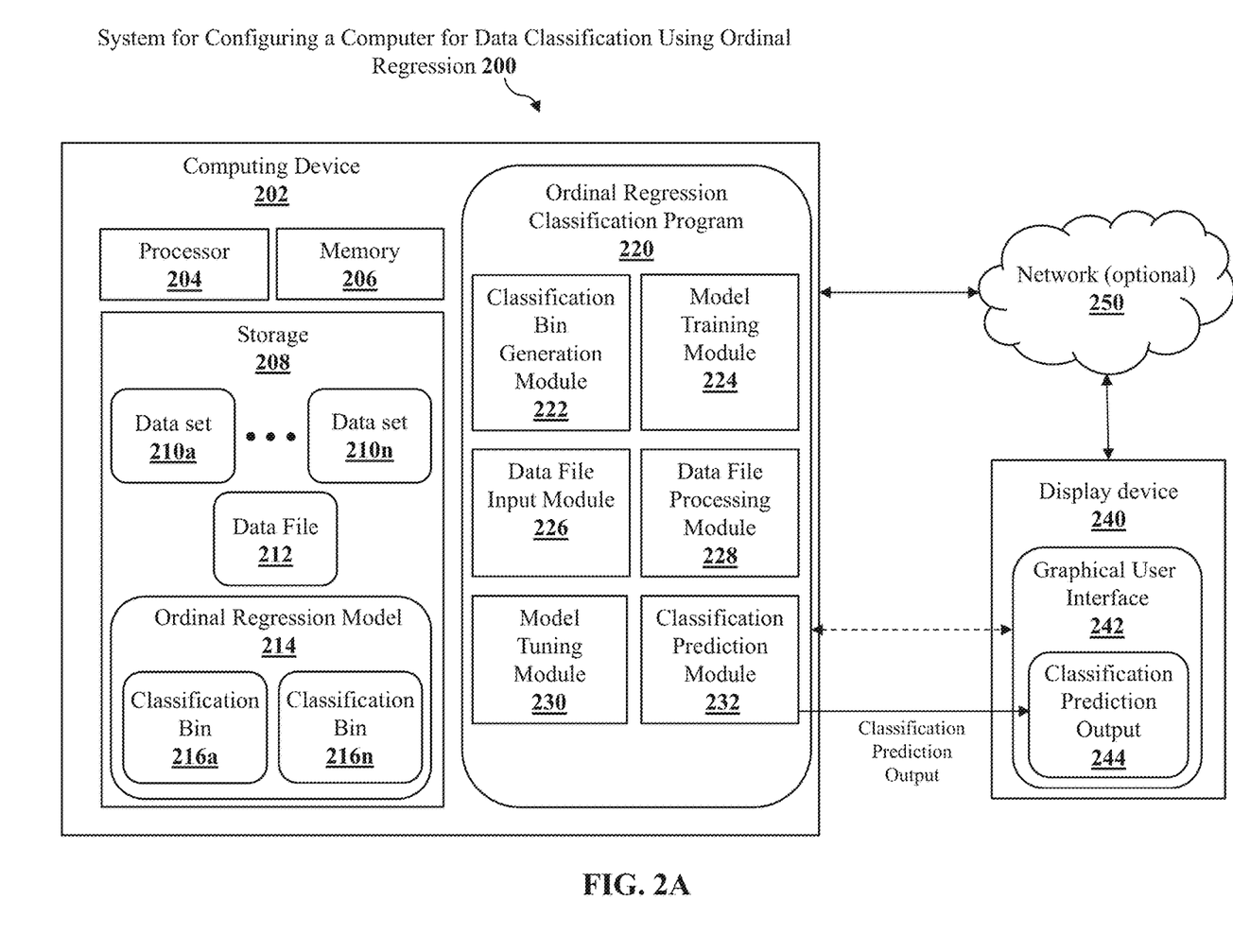
FIG. 2A is a block diagram illustrating a high-level system architecture for configuring a computer for data classification using ordinal regression in accordance with exemplary embodiments.

FIG. 2A illustrates system 100 for configuring a computer for data classification using ordinal regression in accordance with exemplary embodiments.

The computing device 202 includes, for example, a processor 204, a memory 206, a storage 208, and an ordinal regression classification program 220. The device 202 may be a desktop computer, a notebook, a laptop computer, a tablet computer, a handheld device, a smart-phone, a thin client, or any other electronic device or computing system capable of storing, compiling, and organizing audio, visual, or textual data and receiving and sending that data to and from other computing devices, such as the display device 240.

The processor 204 may be a special purpose or a general purpose processor device specifically configured to perform the functions discussed herein. The processor 204 unit or device as discussed herein may be a single processor, a plurality of processors, or combinations thereof. Processor devices may have one or more processor "cores." In an exemplary embodiment, the processor 204 is configured to perform the functions associated with the modules of the ordinal regression classification program 220 as discussed below with reference to FIGS. 2A, 2B, and 3.

The memory 206 can be a random access memory, read-only memory, or any other known memory configurations. Further, the memory 206 can include one or more additional memories including the storage 208 in some embodiments. The memory 206 and the one or more additional memories can be read from and/or written to in a well-known manner. In an embodiment, the memory and the one or more additional memories can be non-transitory computer readable recording media. Memory semiconductors (e.g., DRAMs, etc.) can be means for providing software to the computing device such as the ordinal regression classification program 220. Computer programs, e.g., computer control logic, can be stored in the memory 106.

The storage 208 can include, for example, data sets 210a-210n, a data file 212, and ordinal regression model 214. The storage 208 can be deployed on one or more nodes, e.g., storage or memory nodes, or more processing-capable nodes such as a server computer, desktop computer, notebook computer, laptop computer, tablet computer, handheld device, smart-phone, thin client, or any other electronic device or computing system capable of storing, compiling, and/or processing data and computer instructions (e.g., data sets 210a-210n, a data file 212, and ordinal regression model 214), and receiving and sending that data to and from other devices, such as the display device 240. The storage 208 can be any suitable storage configuration, such as, but not limited to, a relational database, a structured query language (SQL) database, a distributed database, or an object database, etc. Suitable configurations and storage types will be apparent to persons having skill in the relevant art.

The data sets 210a-210n may be any known or generated ordinal data set. Each data set 210 may include any number of data samples having any number of features and any number of classes or ordered categories. For example, the data sets 210a-210n may include one or more of the following data sets in Table 1:

TABLE 1

| Dataset | Samples | Features | Classes |
| --- | --- | --- | --- |
| ERA | 1000 | 4 | 9 |
| ESL | 488 | 4 | 9 |
| LEV | 1000 | 4 | 5 |
| SWD | 1000 | 10 | 4 |
| automobile | 205 | 71 | 6 |
| balance-scale | 625 | 4 | 3 |
| bondrate | 57 | 37 | 5 |
| car | 1728 | 21 | 4 |
| contact-lenses | 24 | 6 | 3 |
| eucalyptus | 736 | 91 | 5 |

TABLE 1-continued

| Dataset | Samples | Features | Classes |
| --- | --- | --- | --- |
| newthyroid | 215 | 5 | 3 |
| pasture | 36 | 25 | 3 |
| squash-stored | 52 | 51 | 3 |
| squash-unstored | 52 | 52 | 3 |
| tae | 151 | 54 | 3 |
| toy | 300 | 2 | 5 |
| winequality-red | 1599 | 11 | 6 |

The samples of each data set 210 are the number of data files that make up the data set 210 and may or may not include the data file 212 as discussed in more detail below. The features of each data set 210 may be any characteristic of the data files that make up the data set 210. For example, the data set 210a may be a hypertension data set including health files of patients and the features may include, but are not limited to, patient Body Mass Index (BMI), and alcohol consumption data. The classes of each data set 210 may be classification categories, e.g., classification bins 216a-216n, within which the data files of each data set 210 may be classified into. While a plurality of data sets 210a-210n are illustrated in FIG. 2A, it can be appreciated that the storage 208 can include a single data set 210 or any number of data sets 210.

The data file 212 may be a data file of one or more of the data sets 210a-210n or the data file 212 may be a separate data file. For example, the data file 212 may be a data file of a data set 210 being used to train the ordinal regression model 214. As another example, the data file 212 may be a data file separate from the data set 210 that is input into the ordinal regression model to classify the data file 212. Further, the data file 212 may include a single piece or data, e.g., a single image, or a plurality of pieces of data, e.g., a plurality of images.

The ordinal regression model 214 is a continuously generalized ordinal regression model that classifies data into one or more classification bins 216a-216n. The ordinal regression classification program 220 may generate the ordinal regression model 214 using one or more of the data sets 210a-210n as training data. While only a single ordinal regression model 214 is illustrated, it can be appreciated that any number of ordinal regression models may be stored in the storage 208. For example, each of the data sets 2101-210n may be used to train a separate ordinal regression model 214. The ordinal regression model 214 classifies the data of the data set 210 and/or the data file 212 into one or more classification bins 216a-216n. Continuing with the above hypertensions example, the classification bins 216a-216n may be, but are not limited to, normal, elevated, stage 1, stage 2, and crisis, etc. In the above example, each classification bin 216a-216n may be associated with a particular blood pressure range, for example, normal may be any systolic blood pressure below 120, and elevated may be a systolic blood pressure between 120 and 129, etc. The generation of the ordinal regression model 214 is discussed in more detail below.

Figure 2B:
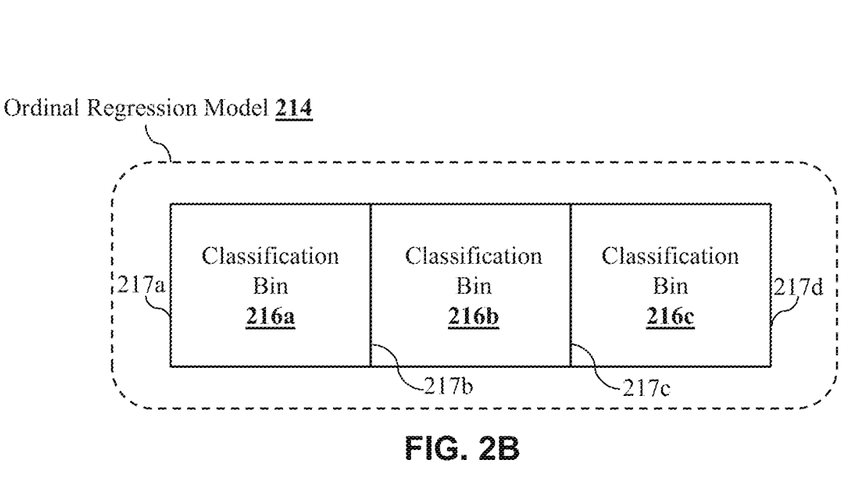
FIG. 2B is a block diagram illustrating an ordinal regression model in accordance with exemplary embodiments.
Figure 2C:
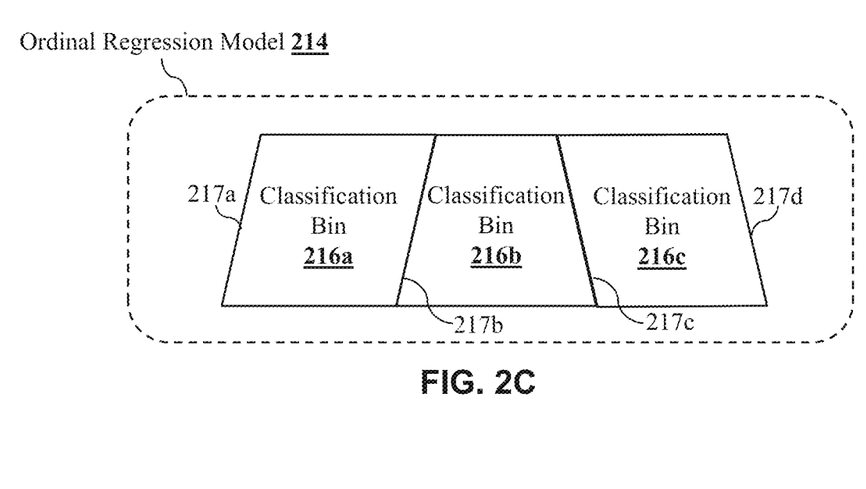
FIG. 2C is a block diagram illustrating an ordinal regression model in accordance with exemplary embodiments.

As discussed above, the ordinal regression model 214 classifies data, e.g., the data file 212, into one or more classification bins 216a-216n of the ordinal classification model 214. Example classification bins 216a-216c are illustrated in FIGS. 2B-2C. Referring to FIG. 2B, the ordinal regression model 214 may contain three classification bins 216a-216c having walls defined by one or more hyperplanes 217a-217d. The ordinal regression classification program 220 generates the hyperplanes 217a-217d based on the relationship between the data of a data set, e.g. one of the data sets 210a-210n. In an exemplary embodiment, the ordinal regression classification program 220 may adjust the slope of the hyperplanes 217a-217d to best fit the data of the data set 210a-21-n that was used to train the ordinal regression model 214. For example, the ordinal regression classification program 220 may adjust the slopes of the hyperplanes 217a-217d from substantially parallel as illustrated in FIG. 2B to having differing slopes as illustrated in FIG. 2C. The generation and adjustment of the classification bins 216a-216n and the hyperplanes 217 are discussed in more detail below with reference to FIG. 3.

The ordinal regression classification program 220 is a software component that utilizes the data sets 210a-210n stored in the storage 208 to generate the ordinal classification model 214 and then classify data, e.g., the data file 212, utilizing the ordinal regression model 214. In an exemplary embodiment, the ordinal regression classification program 220 includes a classification bin generation module 222, a model training module 224, a data file input module 226, a data file processing module 228, a model tuning module 230, and a classification prediction module 232. The ordinal regression classification program 220 is a software component specifically programmed to implement the methods and functions disclosed herein for configuring a computer for data classification using ordinal regression. The ordinal regression classification program 220 and the modules 222-232 are discussed in more detail below with reference to FIG. 3.

The ordinal regression classification program 220 can include a graphical user interface 242. The graphical user interface 242 can include components used to receive input from the computing device 202, and/or the display device 240 and transmit the input to the ordinal regression classification program 220 or conversely to receive information from the ordinal regression classification program 220 and display the information on the computing device 202, and/or the display device 240. In an example embodiment, the graphical user interface 242 uses a combination of technologies and devices, such as device drivers, to provide a platform to enable users of the computing device 202, and/or the display device 240 to interact with the ordinal regression classification program 220. In the example embodiment, the graphical user interface 242 receives input from a physical input device, such as a keyboard, mouse, touchpad, touchscreen, camera, microphone, etc. In an exemplary embodiment, the graphical user interface 242 may display a classification prediction output 244 that indicates a classification on the data file 212. While the graphical user interface 242 is illustrated as part of the display device 240, it can be appreciated that the graphical user interface 242 is a part of the ordinal regression classification program 220 and may be a part of the computing device 202, and/or the display device 240.

While the processor 204, the memory 206, the storage 208, and the ordinal regression classification program 220 are illustrated as part of the computing device 202, it can be appreciated that each of these elements or a combination thereof can be a part of a separate computing device.

The display device 240 can include the graphical user interface 242. The display device 240 be any computing device, such as, but not limited to, a cell phone, a server computer, a desktop computer, a notebook, a laptop computer, a tablet computer, a handheld device, a smart-phone, a thin client, or any other electronic device or computing system capable of receiving display signals from another computing device, such as the computing device 202, etc.

and outputting those display signals to a display unit such as, but not limited to, an LCD screen, plasma screen, LED screen, DLP screen, CRT screen, etc. For example, the graphical user interface 242 may receive the classification prediction output 244 from the ordinal regression classification program 220 and display the classification prediction output 244 on the display device 240. Further, the graphical user interface may receive data input files, e.g., the data file 212, from a user and transmit those data input files, e.g., the data file 212, to the ordinal regression classification program 220. The data input files e.g., the data file 212, can include a single piece of data (e.g., a single image) or multiple pieces of data (e.g., a plurality images). The display device 240 may communicate with the computing device 202 via a hard-wired connection or via the network 250. For example, the display device 240 may have a hard-wired connection to the image device such as, but not limited to, a USB connection, an HDMI connection, a display port connection, a VGA connection, or any other known hard-wired connection capable of transmitting and/or receiving data between the computing device 202 and the display device 240. While the display device 240 is illustrated as being separate from the computing device 202, it can be appreciated that the display device 240 can be a part of the computing device 202.

The optional network 250 may be any network suitable for performing the functions as disclosed herein and may include a local area network (LAN), a wide area network (WAN), a wireless network (e.g., WiFi), a personal area network (PAN) (e.g. Bluetooth), a near-field communication (NFC) network, a mobile communication network, a satellite network, the Internet, fiber optic, coaxial cable, other hardwired networks, infrared, radio frequency (RF), or any combination of the foregoing. Other suitable network types and configurations will be apparent to persons having skill in the relevant art. In general, the network 250 can be any combination of connections and protocols that will support communications between the computing device 202 and the display device 240. In some embodiments, the network 250 may be optional based on the configuration of the computing device 202, and the display device 240.

Figure 3:
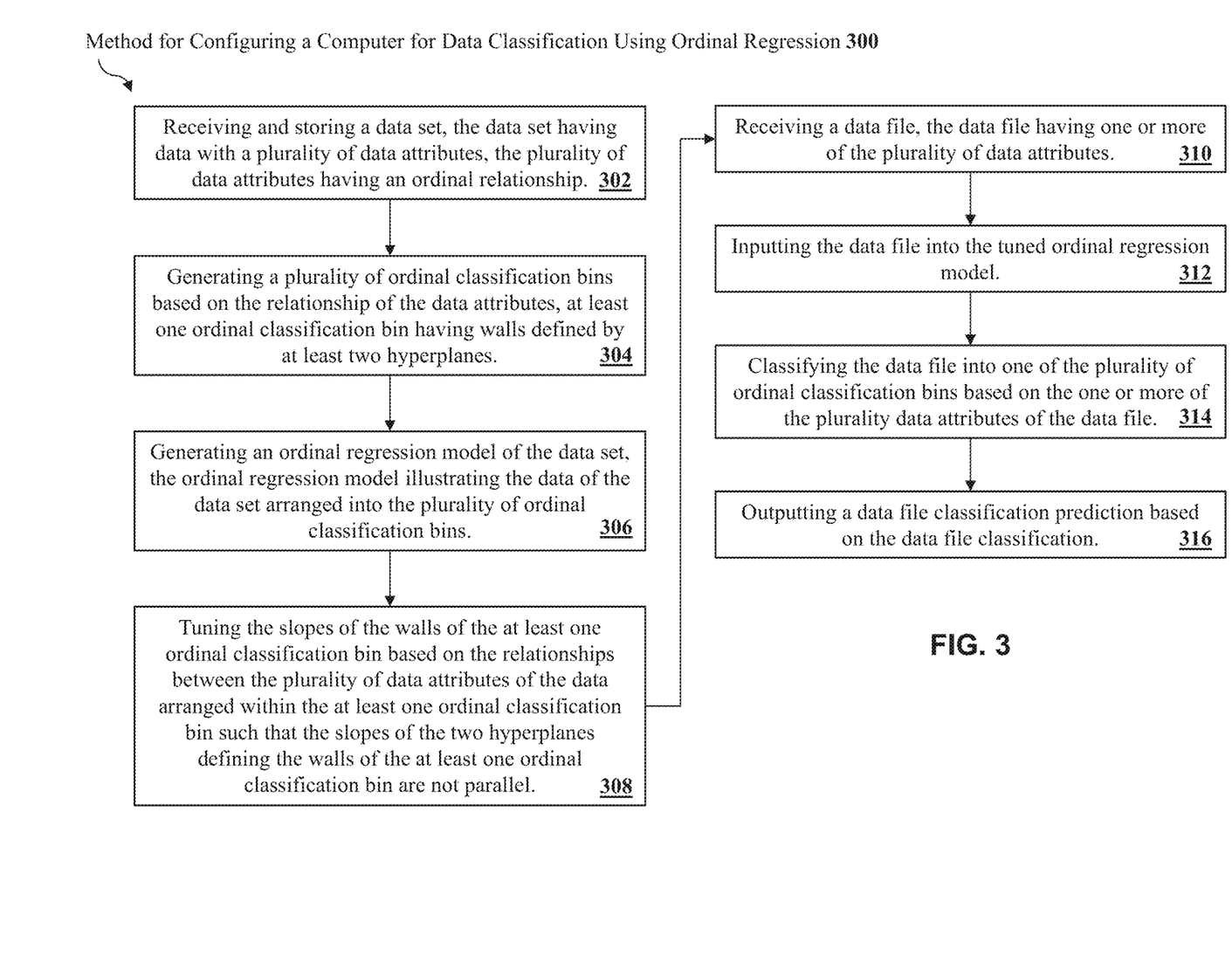
FIG. 3 is a flowchart illustrating a method for configuring a computer for data classification using ordinal regression in accordance with exemplary embodiments.

Exemplary Method for Configuring a Computer for Data Classification Using Ordinal Regression FIG. 3 illustrates a method 300 for configuring a computer for data classification using ordinal regression in accordance with exemplary embodiments.

The method 200 can include block 302 of storing a data set 210, e.g., one or more of the data sets 210a-210n, in the storage 208. Each of the data sets 210a-210n may be made up of data sets of x and y. In an exemplary embodiment x is defined an n number of data files, denoted x, with a plurality data features, denoted p. In an exemplary embodiment, the plurality of data features p have an ordinal relationship. In an exemplary embodiment y is defined an n number of labels among a number k of ordered categories, e.g., the classification bins 216a-216n.

The method 300 can include block 304 of generating a plurality of ordinal classification bins, e.g., the classification bins 216a-216n, based on the relationship of the data features p of the data set 210. The classification bins 216a-216n have one or more walls defined by one or more hyperplanes, e.g. the hyperplanes 217 of FIGS. 2B and 2C. The ordinal regression classification program 220. For example, but not limited to, the classification bins 216a-216n may be systolic blood pressure ranges for categories of hypertension, radio frequency ranges associated with a Quadrature Amplitude Modulation (QAM), disease classifications, pain level ratings, medication dosages, consumer ratings on products, benign vs. malicious software, food categories, plant categories, or any other data classification categories, etc. In an exemplary embodiment, the classification bin generation module 222 can be configured to execute the method of block 304.

The method 300 can include block 306 of generating an ordinal regression model 214 of the data set, e.g., one or more of the data sets 210a-210n. The ordinal regression model 214 illustrates the data of the data set, e.g., one or more of the data sets 210a-210n, arranged into the classification bins 216a-216n. The ordinal regression model 214 may be generated using the linear regression all-thresholds loss function:

$$l(y, f(x)) = \sum_{j=1}^{y-1} \varphi(-g_j(x)) + \sum_{j=y}^{k-1} \varphi(g_j(x)) \quad \text{(Equation 1)}$$

In equation 1, the features p of the data files x can be represented as $x \in \mathbb{R}^p$ and an ordered target variable y is defined using equation 2 below where w is a weight vector for each classification bin 216a-216n:

$$\mathbb{P}(y \leq j|x) = \frac{\exp(\theta_j - w^T x)}{1 + \exp(\theta_j - w^T x)} \quad \text{(Equation 2)}$$

The goal is to learn a decision function ($f: \mathbb{R}^p \to \mathbb{R}$) that minimizes the risk $\mathcal{L}(f) = E(\ell(y, f(x))$ under some loss function $\ell$. Linear ordinal regression models restrict $f$ to the set of parallel linear models $\{g(x; w; \theta)\}$ where $g_j(x) = \theta_j - w^T x$ with bias terms $\theta \in \mathbb{R}^{k-1}$ such that $\theta_1 \leq \ldots \leq \theta_{k-1}$. That is, the linear ordinal regression model is a set of (k−1) thresholds that partition the linear output $w^T x$ into the ordinal classes, e.g., the classification bins 216a-216n. The linear regression model then predicts the number of thresholds crossed. Equation 1 results in the ordinal regression model 214 having classification bins 216a-216n with parallel hyperplanes as in FIGS. 1A and 2B. In an exemplary embodiment, the model training module 224 can be configured to execute the method of block 306.

The method 300 can include block 308 of tuning the slopes of the walls of at least one of the ordinal classification bins 216a-216n based on the relationships between the plurality of data features of the data arranged within each of the classification bins 216a-216n. For example, tuning the slopes of the walls adjusts the allowed slack of the slopes, e.g., the bounds within which the slopes are allowed to deviate from being parallel to each other. In an exemplary embodiment, the slopes of the two hyperplanes defining the walls of the at least one classification bin 216 are not parallel to each other. The ordinal regression classification program 220 may tune the walls of the classification bins 216a-216n by defining a grid of possible α and β values where α is an L2 regularization parameter that controls weights that are assigned to each of the classification bins 216a-216n and β is a term that adjusts the slopes, i.e., controls the size of deviations allowed for the weights, of the hyperplanes 217 defining the walls of the classification bins 216a-216n. For example, the grid may pre-define a set of allowed values for both α, e.g., {0, 1, 5}, and β, e.g., {0, 0.01, 0.05, 0.1, 0.5}. Once the grid has been defined, the ordinal regression classification program 220 cross-validates each possible combination of α and β from the grid to find an optimal α and β for generating the hyperplanes of the classification bins 216a-216n. Cross-validation involves inputting the terms x, y, α, and β along with assigned weights (w) for each data feature (p), and assigned weight deviations (δ) for each data feature p and pair of contiguous categories, e.g., classification bins 216a-216n, into the following equation, i.e., the coGOL equation:

$$l(y, f(x)) = \sum_{j=1}^{y-1} \varphi(-\tilde{g}_j(x)) +$$ (Equation 3)

$$\sum_{j=y}^{k-1} \varphi(\tilde{g}_j(x)) + \underbrace{\alpha\|w\|_2^2}_{standard L2 penalty} + \underbrace{\beta\sum_{j=1}^{k-1}\|\delta_j\|_2^2}_{our deviation penalty}$$

Equation 3 returns the loss function for each α and β combination. Choosing the smallest loss value over the combinations gives the optimal α and β values for the ordinal regression model 214. The ordinal regression classification program 220 then uses the optimal values for α and β in Equation 3 to determine the weights (w), deviations (δ) and θ that most minimize the loss. The optimal α and β and determined weights (w), deviations (δ) and θ are then used to generate a tuned ordinal regression model 214. In an exemplary embodiment, the model tuning module 230 can be configured to execute the method of block 308.

The method 300 can include block 310 of receiving a data file 212. The ordinal regression classification program 220 may receive the data file 212, for example, but not limited to, from a user of the computing device 202 and/or the display device 240, e.g., via the graphical user interface 242, from the storage 208, and/or from the memory 206. The data file 212 may have one or more of the plurality of data features of the data set 210 used to train the ordinal regression model 214. For example, but not limited to, the data file 212 may be a patient's health data containing the features such as the patient's BMI and alcohol consumption data, which may be input into the ordinal classification model 214 to classify the patient's hypertension risk category. In an exemplary embodiment, the data input module 226 can be configured to execute the method of block 310.

The method 300 can include block 312 of classifying the data file 212 into one of the classification bins 216a-216n based on the data features of the data file 212. In order to determine which classification bin 216a-216n to classify the data file 212 into, the ordinal regression model 214 will compute for each classification bin 216a-216n, where j represents each of the classification bins 216a-216: $\tilde{g}_j(x) = \theta_j - (\tilde{w} + \delta_j)^T x$. The number of sums $g_j$ that are negative indicates which classification bin 216a-216n is predicted for the data file 212:

$$f(x) = 1 + \sum_{j=1}^{k-1} [\![ g_j(x) < 0 ]\!]$$ (Equation 4)

In an exemplary embodiment, the data file processing module 228 can be configured to execute the method of block 314.

The method 300 can include block 314 of outputting a classification prediction output 244 for the data file 212 based on the classification of the data file 212. The ordinal regression classification program 220 may output the classification prediction output 244 to a user via the graphical user interface 242 on the display 240 and/or the computing device 202. In an exemplary embodiment, the classification prediction module 232 can be configured to execute the method of block 314.

It can be appreciated that blocks 302-308 of the method 300 can represent the training of the ordinal regression model 214 capable of generating one or more classification bins 216a-216n based on the relationship between the data of a data set, e.g., one of the data sets 210a-210n. Further, it can be appreciated that blocks 310-314 of the method 300 can represent utilizing the trained ordinal regression model 214 on a new data file, e.g., the data file 212.

In addition to the data sets 210a-210n, the ordinal regression classification program 220 can be applied to deep learning such as, but not limited to, neural networks. The ordinal classification model 214 can be used as a final linear layer in a neural network. In use with deep learning, the ordinal regression classification program 220 can replace x (the data of the data sets 210a-210n) with the output of a base neural network F(x) with k−1 independent weight vectors (w) and k−1 biases (δ). The ordinal regression classification program 220 performs steps 302-308 to train the ordinal regression model 214 using Equation 3. For deep learning applications, equation 3 may using deep learning notation as follows:

$$l(y, f(x)) = -\sum_{j=1}^{y-1} \log\sigma(-\tilde{g}_j(F(x))) -$$ (Equation 5)

$$\sum_{j=y}^{k-1} \log\sigma(\tilde{g}_j(F(x))) + \beta\sum_{j=1}^{k-1}\|\delta_j\|_2^2$$

A person having ordinary skill in the art would appreciate that embodiments of the disclosed subject matter can be practiced with various computer system configurations, including multi-core multiprocessor systems, minicomputers, mainframe computers, computers linked or clustered with distributed functions, as well as pervasive or miniature computers that can be embedded into virtually any device. For instance, one or more of the disclosed modules can be a hardware processor device with an associated memory.

A hardware processor device as discussed herein can be a single hardware processor, a plurality of hardware processors, or combinations thereof. Hardware processor devices can have one or more processor "cores." The term "non-transitory computer readable medium" as discussed herein is used to generally refer to tangible media such as a memory device.

Various embodiments of the present disclosure are described in terms of an exemplary computing device. After reading this description, it will become apparent to a person skilled in the relevant art how to implement the present disclosure using other computer systems and/or computer architectures. Although operations can be described as a sequential process, some of the operations can in fact be performed in parallel, concurrently, and/or in a distributed environment, and with program code stored locally or remotely for access by single or multiprocessor machines. In addition, in some embodiments the order of operations can be rearranged without departing from the spirit of the disclosed subject matter.

A system, as used herein, can be in combination with one or more nodes, wherein the system resides in the one or more nodes. A node can be configured to interface or contain one or more components of the systems described herein.

A hardware processor, as used herein, can be a special purpose or general purpose processor device. The hardware processor device can be connected to a communications infrastructure, such as a bus, message queue, network, multi-core message-passing scheme, etc. An exemplary computing device, as used herein, can include a memory (e.g., random access memory, read-only memory, etc.), and can also include one or more additional memories. The memory and the one or more additional memories can be read from and/or written to in a well-known manner. In an embodiment, the memory and the one or more additional memories can be non-transitory computer readable recording media.

Data stored in the exemplary computing device (e.g., in the memory) can be stored on any type of suitable computer readable media, such as optical storage (e.g., a compact disc, digital versatile disc, Blu-ray disc, etc.), magnetic tape storage (e.g., a hard disk drive), solid-state drive, etc. An operating system can be stored in the memory.

In an exemplary embodiment, the data can be configured in any type of suitable data storage configuration or database configuration, such as a relational database, a structured query language (SQL) database, a distributed database, an object database, etc. Suitable configurations and storage types will be apparent to persons having skill in the relevant art.

The exemplary computing device can also include a communications interface. The communications interface can be configured to allow software and data to be transferred between the computing device and external devices. Exemplary communications interfaces can include a modem, a network interface (e.g., an Ethernet card), a communications port, a PCMCIA slot and card, etc. Software and data transferred via the communications interface can be in the form of signals, which can be electronic, electromagnetic, optical, or other signals as will be apparent to persons having skill in the relevant art. The signals can travel via a communications path, which can be configured to carry the signals and can be implemented using wire, cable, fiber optics, a phone line, a cellular phone link, a radio frequency link, etc.

Memory semiconductors (e.g., DRAMs, etc.) can be means for providing software to the computing device. Computer programs (e.g., computer control logic) can be stored in the memory. Computer programs can also be received via the communications interface. Such computer programs, when executed, can enable the computing device to implement the present methods as discussed herein. In particular, the computer programs stored on a non-transitory computer-readable medium, when executed, can enable a hardware processor device to implement the exemplary methods, or similar methods, as discussed herein. Accordingly, such computer programs can represent controllers of the computing device.

Where the present disclosure is implemented using software, the software can be stored in a computer product or non-transitory computer readable medium and loaded into the computing device using a removable storage drive or communications interface. In an exemplary embodiment, any computing device disclosed herein can also include a display interface that outputs display signals to a display unit, e.g., LCD screen, plasma screen, LED screen, DLP screen, CRT screen, etc.

It will be appreciated by those skilled in the art that the present disclosure can be embodied in other specific forms without departing from the spirit or essential characteristics thereof. The presently disclosed embodiments are therefore considered in all respects to be illustrative and not restrictive. The scope of the disclosure is indicated by the appended claims rather than the foregoing description, and all changes that come within the meaning, range, and equivalence thereof are intended to be embraced therein.

What is claimed is:

1. A method for configuring a computer for data classification using ordinal regression, the method comprising:
storing, in memory, program code for performing an ordinal regression classification;
executing, by processor of the computer, the program code to perform the operations including:
receiving and storing a data set, the data set having data with a plurality of data features, the plurality of data features having an ordinal relationship;
generating a plurality of ordinal classification bins based on the relationship of the data features, at least one ordinal classification bin having walls defined by at least two hyperplanes;
generating an ordinal regression model of the data set, the ordinal regression model illustrating the data of the data set arranged into the plurality of ordinal classification bins; and
tuning the slopes of the walls of the at least one ordinal classification bin based on the relationships between the plurality of data features of the data arranged within the at least one ordinal classification bin such that the slopes of the two hyperplanes defining the walls of the at least one ordinal classification bin are not parallel, wherein the walls of the slopes of the two hyperplanes are tuned by controlling weights that are assigned to the at least one classification bin and controlling a size of deviations allowed for the weights assigned to the at least one classification bin.

2. The method of claim 1, comprising:
receiving a data file, the data file having one or more of the plurality of data features;
inputting the data file into the tuned ordinal regression model;
classifying the data file into one of the plurality of ordinal classification bins based on the one or more of the plurality data features of the data file; and
outputting a data file classification prediction based on the data file classification.

3. The method of claim 1, wherein the tuning of the slopes of the walls includes cross-validating the ordinal regression model using one or more subsets of data of the data set.

4. The method of claim 1, wherein the tuning of the slopes of the walls includes adjusting the allowed slack of the slopes.

5. The method of claim 1, wherein the generating of the ordinal regression model includes training the ordinal regression model using the data set and a generalized coefficient for each of the plurality of data features.

6. The method of claim 1, the plurality of data features includes health information and each of the one or more ordinal classification bins is a hypertension risk category.

7. The method of claim 1, the plurality of data features includes radio frequency signals and each of the one or more ordinal classification bins is a radio frequency channel.

8. The method of claim 1, wherein tuning the slopes of the walls of the at least one ordinal classification bin includes:
defining a grid of regularization parameters and slope deviation values, the regularization parameters controlling the weights that are assigned to each of the plurality of ordinal classification bins, and the slope deviation values controlling the size of deviations allowed for the weights defining the walls of the plurality of ordinal classification bins.

9. The method of claim 8, further comprising:
cross-validating all combinations of regularization parameters and slope deviation values from the grid to select a regularization parameter and a slope deviation value which generate a smallest loss value; and
generating the hyperplanes of the plurality of classification bins using the selected regularization parameter and slope deviation value.

10. The method of claim 1, wherein the ordinal regression model is a final layer in a neural network.

11. A system for configuring a computer for data classification using ordinal regression, the system comprising:
a memory configured to:
store program code for performing an ordinal regression classification; and
receive and store a data set, the data set having data with a plurality of data features, the plurality of data features having an ordinal relationship; and
a processor configured to:
execute the program code such that the processor is further configured to:
generate a plurality of ordinal classification bins based on the relationship of the data features, at least one ordinal classification bin having walls defined by at least two hyperplanes;
generate an ordinal regression model of the data set, the ordinal regression model illustrating the data of the data set arranged into the plurality of ordinal classification bins;
tune the slopes of the walls of the at least one ordinal classification bin based on the relationships between the plurality of data features of the data arranged within the at least one ordinal classification bin such that the slopes of the two hyperplanes defining the walls of the at least one ordinal classification bin are not parallel, wherein the slopes of the walls of the two hyperplanes are tuned by controlling weights that are assigned to the at least one classification bin and controlling a size of deviations allowed for the weights assigned to the at least one classification bin.

12. The system of claim 11, comprising:
the processor configured to:
receive a data file, the data file having one or more of the plurality of data features;
input the data file into the tuned ordinal regression model;
classify the data file into one of the plurality of ordinal classification bins based on the one or more of the plurality data features of the data file; and
output a data file classification prediction based on the data file classification.

13. The system of claim 11, wherein the tuning of the slopes of the walls includes cross-validating the ordinal regression model using one or more subsets of data of the data set.

14. The system of claim 11, wherein the tuning of the slopes of the walls includes adjusting the allowed slack of the slopes.

15. The system of claim 11, wherein the generating of the ordinal regression model includes training the ordinal regression model using the data set and a generalized coefficient for each of the plurality of data features.

16. The system of claim 11, the plurality of data features includes health information and each of the one or more ordinal classification bins is a hypertension risk category.

17. The system of claim 11, the plurality of data features includes radio frequency signals and each of the one or more ordinal classification bins is a radio frequency channel.

18. The system of claim 11, wherein tuning the slopes of the walls of the at least one ordinal classification bin includes:
the processor configured to:
define a grid of regularization parameters and slope deviation values, the regularization parameters controlling the weights that are assigned to each of the plurality of ordinal classification bins, and the slope deviation values controlling the size of deviations allowed for the weights defining the walls of the plurality of ordinal classification bins.

19. The system of claim 18, wherein the processor is further configured to:
cross-validate all combinations of regularization parameters and slope deviation values from the grid to select a regularization parameter and a slope deviation value which generate a smallest loss value; and
generate the hyperplanes of the plurality of classification bins using the selected regularization parameter and slope deviation value.

20. The system of claim 11, wherein the ordinal regression model is a final layer in a neural network.

* * * * *